(12) United States Patent
Laugere et al.

(10) Patent No.: US 10,004,849 B2
(45) Date of Patent: Jun. 26, 2018

(54) DISPENSE INTERFACE FOR AN EJECTION DEVICE

(71) Applicant: Sanofi-Aventis Deutschland GmbH, Frankfurt am Main (DE)

(72) Inventors: Frederic Laugere, Bedfordshire (GB); Cristian Popa, Norfolk (GB); Ben Impey, Cambridgeshire (GB); Andrew MacLeod, Cambridgeshire (GB)

(73) Assignee: Sanofi-Aventis Deutschland GmbH, Frankfurt on the Main (DE)

( * ) Notice: Subject to any disclaimer, the term of this patent is extended or adjusted under 35 U.S.C. 154(b) by 463 days.

(21) Appl. No.: 14/397,827

(22) PCT Filed: May 16, 2013

(86) PCT No.: PCT/EP2013/060156
§ 371 (c)(1),
(2) Date: Oct. 29, 2014

(87) PCT Pub. No.: WO2013/171306
PCT Pub. Date: Nov. 21, 2013

(65) Prior Publication Data
US 2015/0126961 A1 May 7, 2015

(30) Foreign Application Priority Data

May 16, 2012 (EP) .................................... 12168366

(51) Int. Cl.
*A61M 5/19* (2006.01)
*A61M 5/315* (2006.01)
(Continued)

(52) U.S. Cl.
CPC .......... *A61M 5/19* (2013.01); *A61M 5/31596* (2013.01); *A61M 5/2448* (2013.01);
(Continued)

(58) Field of Classification Search
CPC ................ A61M 5/19; A61M 5/31596; A61M 2005/1787; A61M 2005/2403;
(Continued)

(56) References Cited

U.S. PATENT DOCUMENTS 1,704,921 A * 3/1929 Nicoll ..................... A61M 5/24
604/232
4,337,791 A * 7/1982 Tech ................... A61M 39/286
137/556

(Continued)

FOREIGN PATENT DOCUMENTS

CN       1064622 A    9/1992
WO       9411039 A1   5/1994
(Continued)

OTHER PUBLICATIONS

Chinese Search Report for CN Application No. 201380023506.8, dated May 10, 2016.

*Primary Examiner* — Bradley J Osinski
*Assistant Examiner* — Nilay Shah
(74) *Attorney, Agent, or Firm* — McCarter & English, LLP

(57) ABSTRACT

The invention inter alia relates to a dispense interface for an ejection device. The dispense interface comprises at least two inlets, at least one outlet and a part having multiple portions; wherein the multiple portions are connected by living hinges such that the multiple portions are foldable towards each other; wherein the multiple portions are configured to form a fluid channel arrangement between functional surfaces of the multiple portions facing each other when the multiple portions are folded towards each other; wherein at least two functional surfaces of the functional surfaces are inclined to each other when the multiple portions are folded towards each other; and wherein the fluid (Continued)

channel arrangement is configured to provide fluid communication between the at least two inlets and the at least one outlet.

20 Claims, 13 Drawing Sheets

(51) Int. Cl.
 *A61M 5/24* (2006.01)
 *A61M 39/22* (2006.01)
 *A61M 5/178* (2006.01)
(52) U.S. Cl.
 CPC ... *A61M 39/223* (2013.01); *A61M 2005/1787* (2013.01); *A61M 2005/2414* (2013.01); *A61M 2207/00* (2013.01); *Y10T 29/49826* (2015.01)
(58) Field of Classification Search
 CPC .. A61M 2005/2414; A61M 2005/2496; A61M 5/2448; A61M 37/00; A61M 5/34; A61M 5/343; A61M 2005/1585
 See application file for complete search history.

(56) References Cited

U.S. PATENT DOCUMENTS

| 5,605,255 | A | * | 2/1997 | Reidel | A61B 17/00491 |
|  |  |  |  |  | 222/137 |
| 6,280,420 | B1 | * | 8/2001 | Ferguson | A61M 5/3275 |
|  |  |  |  |  | 604/192 |
| 2003/0120217 | A1 |  | 6/2003 | Abergel |  |

FOREIGN PATENT DOCUMENTS

| WO |  | 9917933 A1 |  | 4/1999 |  |  |
| WO | WO | 9917833 A1 | * | 4/1999 | ....... | B05C 17/00553 |

* cited by examiner

DISPENSE INTERFACE FOR AN EJECTION DEVICE

CROSS REFERENCE TO RELATED APPLICATIONS

The present application is a U.S. National Phase Application pursuant to 35 U.S.C. § 371 of International Application No. PCT/EP2013/060156 filed May 16, 2013, which claims priority to European Patent Application No. 12168366.8 filed May 16, 2012. The entire disclosure contents of these applications are herewith incorporated by reference into the present application.

FIELD OF INVENTION

The present patent application relates to medical devices for delivering at least two drug agents from separate reservoirs. Such drug agents may comprise a first and a second medicament. The medical device includes a dose setting mechanism for delivering the drug agents automatically or manually by the user.

BACKGROUND

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agents may be contained in two or more multiple dose reservoirs, containers or packages, each containing independent (single drug compound) or pre-mixed (co-formulated multiple drug compounds) drug agents.

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

SUMMARY

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.

5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.

6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections.

The invention inter-alia faces the technical problem of providing a simple dispense interface for an ejection device that is easy to manufacture.

According to a first aspect of the invention, a dispense interface for an ejection device comprises at least two inlets, at least one outlet and a part having multiple portions;

wherein the multiple portions are connected by living hinges such that the multiple portions are foldable towards each other; wherein the multiple portions are configured to form a fluid channel arrangement between functional surfaces of the multiple portions facing each other when the multiple portions are folded towards each other; wherein at least two functional surfaces of the functional surfaces are inclined to each other when the multiple portions are folded towards each other; and wherein the fluid channel arrangement is configured to provide fluid communication between the at least two inlets and the at least one outlet.

The ejection device may be a drug delivery device such as a medical device configured to eject a drug agent (e.g. a dose of a medicament) such as an infusion device or an injection device, for instance an insulin injection pen. Injection devices may be used either by medical personnel or by patients themselves. As an example, type-1 and type-2 diabetes may be treated by patients themselves by injection of insulin doses, for example once or several times per day. In particular, the ejection device may be a medical device configured to deliver (e.g. eject) at least two drug agents from separate reservoirs.

Alternatively, the ejection device may for instance be configured to deliver (e.g. eject) a two-component adhesive from separate fluid reservoirs comprising a first component of the two-component adhesive (e.g. a binder) and a second component of the two-component adhesive (e.g. a hardener), respectively.

The dispense interface may be a disposable part attachable to the ejection device (e.g. the medical device). In particular, the dispense interface may be a single-use part attachable to the ejection device. Each of the at least two inlets of the dispense interface may be configured to reside in fluid communication with one of at least two separate fluid reservoirs of the ejection device when the dispense interface is attached to the ejection device.

The ejection device and/or the dispense interface may preferably be portable (e.g. handheld) devices.

The fluid channel arrangement may provide a fluid connection between each of the at least two inlets of the dispense interface and the at least one outlet of the dispense interface. Also, the fluid channel arrangement may provide a fluid connection between the at least two inlets of the dispense interface. For instance, the fluid channel arrangement is at least partially Y-like, T-like or Z-like shaped.

The fluid channel arrangement may comprise one or more connected fluid channels. The diameter of the fluid channels may be between 0.01 mm and 10 mm. In particular, the diameter of the fluid channels may be between 0.1 mm and 1 mm, for instance about 0.3 mm. The ratio between the length of the fluid channel arrangement and the diameter of the fluid channels (length:diameter ratio) may be substantially large, for instance between 10:1 and 1000:1. In particular, the length:diameter ratio may be between 20:1 and 100:1, for instance about 33:1 or 66:1. The length of the fluid channel arrangement may preferably describe the longest fluid path of the fluid channel arrangement.

Integrally formed parts having a fluid channel arrangement with a substantially large ratio between the length of the fluid channel arrangement and the diameter of the fluid channels (length:diameter ratio) cannot be simply manufactured, for instance by moulding such as injection moulding. This is inter-alia due to the fact that the fluid channel arrangement is difficult to access. Complex tooling is necessary to manufacture such parts.

Since the fluid channel arrangement of the dispense interface of the first aspect of the invention is formed between functional surfaces of the multiple portions facing each other when the multiple portions are folded towards each other, manufacturing thereof is simplified. The functional surfaces of the multiple portions are easily accessible.

The part having the multiple portions may for instance be manufactured by moulding such as injection moulding, for instance by use of an open-and-shut tool without the need for complex tooling. By joining corresponding portions of the multiple portions after manufacturing thereof, it is thus possible to form a joined part having fluid channels with a large length:diameter ratio and/or a complex geometry and/or tight tolerances. For instance, the multiple portions may comprise at least two body portions and at least two cover portions. Each of the body portions may correspond to one of the cover portions.

The fluid channel arrangement may at least substantially be arranged in a sectional plane of the dispense interface. In particular, the sectional plane may for instance be inclined to contact/mating areas of the functional surfaces of the multiple portions when the multiple portions are folded towards each other. For instance, the sectional plane may be a vertical plane of the dispense interface and/or a longitudinal plane of the dispense interface. Preferably, the fluid channel arrangement should be understood to be at least substantially arranged in a sectional plane of the dispense interface if at least a predominant portion of the fluid channel arrangement (e.g. more than 50%, preferably more than 75%, and more preferably more than 90%) is cut by the sectional plane of the dispense interface.

Fluid channels of the fluid channel arrangement may only be formed between functional surfaces of the multiple portions, but not all surfaces facing each other when the multiple portions are folded towards each other may be functional surfaces.

As described above, the multiple portions may comprise at least two body portions and at least two cover portions. The fluid channels of the fluid channel arrangement may (only) be formed between functional surfaces of the body portions and functional surfaces of the cover portions facing each other when the multiple portions are folded towards each other. Each of the multiple portions may only have one functional surface. In addition to the fluid channels of the fluid channel arrangement formed between the functional surfaces of the multiple portions facing each other when the multiple portions are folded towards each other, the multiple portions may comprise further fluid channels.

At least two functional surfaces of the functional surfaces are inclined to each other when the multiple portions are folded towards each other. For instance, the functional surface of a first body portion may be inclined to the functional surface of a second neighboring body portion when the multiple portions are folded towards each other. The first and the second body portion may be connected by a living hinge spaced from the functional surfaces. This is inter-alia advantageous to provide a dispense interface with a fluid channel arrangement with a complex geometry (e.g. with inclined fluid channels).

A living hinge may be a flexure bearing connecting two portions of the multiple portions. In particular, the living hinges may be integrally formed with the multiple portions. Accordingly, the living hinges may be made from the same material as the multiple portions. For instance, a living hinge may be formed by a defined pre-weakening of the part having the multiple portions. For instance, a living hinge may at least partially be formed by a thinned portion of the part having the multiple portions, a perforated portion thereof and/or a cut portion thereof. The type of defined pre-weakening may be selected depending on the material and thickness of the part having the multiple portions.

A living hinge may be configured to allow the two portions of the multiple portions connected by the living hinge to bend along the line of the hinge (i.e. the rotational axis of the living hinge) such that the two portions are foldable towards each other.

A living hinge may be arranged next to neighboring surfaces of the multiple portions facing each other when the multiple portions are folded towards each other. For instance, the living hinge may provide a flexible connection between these neighboring surfaces. The living hinge may be arranged at an edge of these neighboring surfaces. For instance, the living hinge may extend along these edges (with or without interruptions).

For instance, each of the living hinges may have a rotational axis that is angled to the sectional plane at least substantially comprising the fluid channel arrangement. As described above, the sectional plane at least substantially comprising the fluid channel arrangement may be a longitudinal plane and/or a vertical plane. Accordingly, the rotational axis may be transversely oriented.

The at least one outlet of the dispense interface may serve as a common outlet for separate fluid reservoirs of the ejection device. As described above, each of these separate fluid reservoirs may reside in fluid communication with one of the at least two inlets of the dispense interface when the dispense interface is attached to the ejection device.

The at least two inlets of the dispense interface and/or the at least one outlet of the dispense interface may be either arranged in one or more of the multiple portions or between facing surfaces of the multiple portions. For instance, each of the at least two inlets of the dispense interface and/or the at least one outlet of the dispense interface may be formed integrally with multiple portions. Alternatively, the at least two inlets of the dispense interface and/or the at least one outlet of the dispense interface may be subsequently mounted on the multiple portions.

As described above, corresponding portions of the multiple portions may be joining components of the dispense interface. For instance, the corresponding portions of the multiple portions may be configured to be joined by folding the multiple portions towards each other.

During assembly of the dispense interface, the multiple portions may be folded towards each other such that the facing surfaces of the multiple portions contact/mate each other at a contact/mating area, and the multiple portions may fixed in this folded position and/or fitted with further components.

Due to the arrangement of the living hinge, the multiple portions may be manufactured in a single manufacturing step. Furthermore, the count and complexity of assembly parts of the dispense interface is reduced. The invention is therefore inter alia advantageous to allow a simple manufacturing and/or assembly of a dispense interface. Also, it allows provision of a fluid channel arrangement with a complex geometry. Also, it allows a cost-effective manufacturing/assembly of a disposable dispense interface (e.g. a single-use dispense interface).

According to an exemplary embodiment of the dispense interface of the first aspect of the invention, each of the at least two inlets is formed from a fluid connector emptying into the fluid channel arrangement, wherein each of the fluid connectors is configured to establish a releasable fluid connection with a corresponding fluid connector of a fluid reservoir of the ejection device when the dispense interface is attached to the ejection device.

Non-limiting examples of a fluid connector may be a piercing needle, a piercable septum and/or a (male/female) Luer-connector. Such a fluid connector may be integrally formed with the multiple portions. Alternatively, such a fluid connector may at least partially be inserted (e.g. potted/over-moulded/mounted) into the multiple portions. For instance, such a fluid connector may at least partially be potted/over-moulded when the multiple portions are injection moulded. For instance, such a fluid connector may at least partially be glued/mounted in a separate step after the multiple portions have been injection moulded.

According to an exemplary embodiment of the dispense interface of the first aspect of the invention, the at least one outlet is formed from a fluid connector, wherein the fluid channel arrangement empties into the fluid connector, and wherein the fluid connector is configured to establish a fluid connection with a corresponding fluid connector of a (e.g. ejection/injection) needle assembly, when the needle assembly is attached to the dispense interface. The needle assembly may have an injection needle for penetrating the skin of a patient such as a cannula.

As described above, non-limiting examples of a fluid connector may be a piercing needle, a piercable septum and/or a (male/female) Luer-connector. Such a fluid connector may be integrally formed with the multiple portions. Alternatively, such a fluid connector may at least partially be inserted (e.g. potted/over-moulded/mounted) into the multiple portions. For instance, such a fluid connector may at least partially be potted/over-moulded when the multiple portions are injection moulded. For instance, such a fluid connector may at least partially be glued/mounted in a separate step after the multiple portions have been injection moulded.

The fluid connector forming the at least one outlet of the dispense interface, allows to exchange the needle assembly more often than the dispense interface. This is inter-alia advantageous if the needle assembly is a single-use device which has to be replaced after a single ejection and the dispense interface is a disposable part which can be used for more than one ejection.

According to an exemplary embodiment of the dispense interface of the first aspect of the invention, the at least one outlet is formed from a needle, wherein the fluid channel arrangement empties into the needle. The needle may be an injection needle for penetrating the skin of a patient such as a cannula.

The needle may at least partially be inserted (e.g. potted/over-moulded/mounted) into the multiple portions. For instance, the needle may at least partially be potted/over-moulded when the multiple portions are injection moulded. For instance, the needle may at least partially be glued/mounted in a separate step after the multiple portions have been injection moulded. For instance, the needle may be an integral part of the dispense interface.

Since the at least one outlet is already formed from a needle, no attachment of a separate needle assembly is necessary. This embodiment thus inter-alia allows to reduce the overall complexity of the dispense interface and/or the ejection device. This is inter-alia advantageous if the dispense interface is a single use device which has to be replaced after a single ejection.

According to an exemplary embodiment of the dispense interface of the first aspect of the invention, the dispense interface further comprises a valve arrangement configured to control a fluid flow from the at least two inlets to the at least one outlet via the fluid channel arrangement. The valve arrangement may comprise one or more valves, preferably one or more non-return valves. Such a valve arrangement may preferably be configured to prevent cross contamination of fluids contained in separate fluid reservoirs of the ejection device. A preferred valve arrangement may also be configured so as to prevent back flow. Non-limiting examples of such valves are a diaphragm/flap valve, a shuttling valve, a moulded duck bill valve, a flat spring valve and/or a rotating flap valve.

The valve arrangement may for instance be integrally formed with the multiple portions. Alternatively, the valve arrangement may for instance be manufactured separately from the multiple portions. The valve arrangement may be inserted (e.g. potted/over-moulded/mounted) into the multiple portions. For instance, the valve arrangement may at least partially be potted/over-moulded when the multiple portions are injection moulded. For instance, the valve arrangement may at least partially be mounted in a separate step after the multiple portions have been injection moulded.

According to an exemplary embodiment of the dispense interface of the first aspect of the invention, the multiple portions are folded towards each other. In particular, the multiple portions may be folded towards each other such that facing surfaces of the multiple portions contact/mate each other at a contact/mating area. In this folded position, the fluid channel arrangement is formed between the functional surfaces of the multiple portions.

In particular, the multiple portions may be fixed in this folded position by a mechanical connection and/or by a material connection. In particular, the facing surfaces of the multiple portions may at least partially be connected with each other (e.g. at a contact/mating area) by such a mechanical connection and/or by a material connection.

Non-limiting examples of a mechanical connection are a frictional fit, a bolted connection, a rivet connection and/or a clamp connection. For instance, complimentary fastening means may be integrally formed with the multiple portions which are configured to mechanically fix the multiple portions in this folded position. Non-limiting examples of a material connection are glueing, welding (e.g. friction welding, ultrasonic welding and/or laser welding) and/or vulcanizing.

According to an exemplary embodiment of the dispense interface of the first aspect of the invention, the multiple portions comprise at least two body portions and at least two cover portions, wherein each fluid channel of the fluid channel arrangement is formed between a functional surface of a body portion and a functional surface of a cover portion when the multiple portions are folded towards each other. The functional surface of the body portion and the functional surface of the cover portion may face (e.g. contact/mate) each other when the multiple portions are folded towards each other.

According to an exemplary embodiment of the dispense interface of the first aspect of the invention, in each of the functional surfaces of the body portions one or more fluid grooves are arranged. Additionally, also fluid grooves may be arranged in the functional surfaces of the cover portions.

The fluid grooves may be any indentations on the functional surfaces of the body portions (and on the cover portions) which permit the passing of fluid along the functional surfaces thereof. The functional surfaces of the cover portions (and of the body portions) may be configured to (laterally) seal the fluid grooves when the multiple portions are folded towards each other such that a tight fluid channel arrangement is formed.

According to an exemplary embodiment of the dispense interface of the first aspect of the invention, at least one living hinge of the living hinges connecting two body portions of the at least two body portions is spaced from the functional surfaces of these two body portions.

According to an exemplary embodiment of the dispense interface of the first aspect of the invention, the part having the multiple portions is integrally formed by injection moulding (e.g. so-called clam shell moulding). For instance, the multiple portions are formed in a single step by injection moulding by use of an open-and-shut tool.

For instance, use of an open-and-shut tool reduces the need for fragile core pins or split lines with a groove arrangement. This also allows for relatively complex and tight tolerance geometry without complex tooling. The moulding of key assembly snap features on the same component, such as an outer protrusion on a portion, may also helps reduce tolerance stack-ups and also tends to allow for smaller fluid grooves (e.g. needle wells) and therefore smaller ullage.

For instance, polymer materials may be used in injection moulding of the multiple portions. Polymer materials are typically biocompatible. For instance, COP (cyclo-olefin polymer) materials may be used in injection moulding of the multiple portions. COP materials have a high biocompatibility. For instance, COP materials have little to no extractables and most COP materialy can undergo sterilization by gamma radiation, steam and/or ethylene oxide. Other materials such as PP (poly-propylene) or HDPE (high density poly-ethylene) or other less expensive materials may be used, too. Especially, a single use dispense interface may be made from such a material, as the contact time with the medicament is rather short (only the time from priming the device until the injection is completed).

The exemplary embodiment of the dispense interface of the first aspect of the invention thus allows a simple manufacturing of the part having the multiple portions. Furthermore, it allows manufacturing this part from a biocompatible material. Potential problems of material compatibility, absorption and cross contamination between the fluids (e.g. drugs) and the polymer material are overcome by the selection of a biocompatible material and/or—for a single use dispense interface—by a short contact time.

According to a second aspect of the invention, a method for manufacturing a dispense interface of the first aspect of the invention comprises (e.g. injection) moulding a part having multiple portions, folding the multiple portions towards each other; and fixing the multiple portions in this folded position (e.g. by establishing a material connection and/or by establishing a mechanical connection).

According to a third aspect of the invention, a system comprises the dispense interface of the first aspect of the invention and an ejection device, wherein the dispense interface is attached to the ejection device. The system may further comprise a needle assembly, wherein the needle assembly is attached to the dispense interface. The dispense interface may provide a fluid connection between at least two fluid reservoirs of the ejection device and the needle assembly. As described above, the ejection device may be a medical device configured to deliver (e.g. eject) a medicament.

According to a fourth aspect of the invention, a method for using the system of the third aspect of the invention comprises attaching a dispense interface of the first aspect of the invention to an ejection device having at least two fluid reservoirs, ejecting a fluid from at least one of the reservoirs through the dispense interface and detaching the dispense interface from the ejection device. The method may furthermore comprise attaching a needle assembly to the dispense interface, wherein the fluid is ejected from at least one of the reservoirs through the dispense interface out of the needle assembly.

Exemplary features/embodiments (exhibiting further features) of the invention have been described above, which are understood to apply to the various aspects of the invention. These single features/embodiments are considered to be exemplary and non-limiting, and to be respectively combinable independently from other disclosed features of the various aspects of the invention as described above. Nevertheless, these exemplary features/embodiments shall also be considered to be disclosed in all possible combinations with each other and with the various aspects of the invention as described above.

BRIEF DESCRIPTION OF THE DRAWINGS

These as well as other advantages of various aspects of the present invention will become apparent to those of ordinary skill in the art by reading the following detailed description, with appropriate reference to the accompanying drawings, in which.

DETAILED DESCRIPTION

Figure 1:
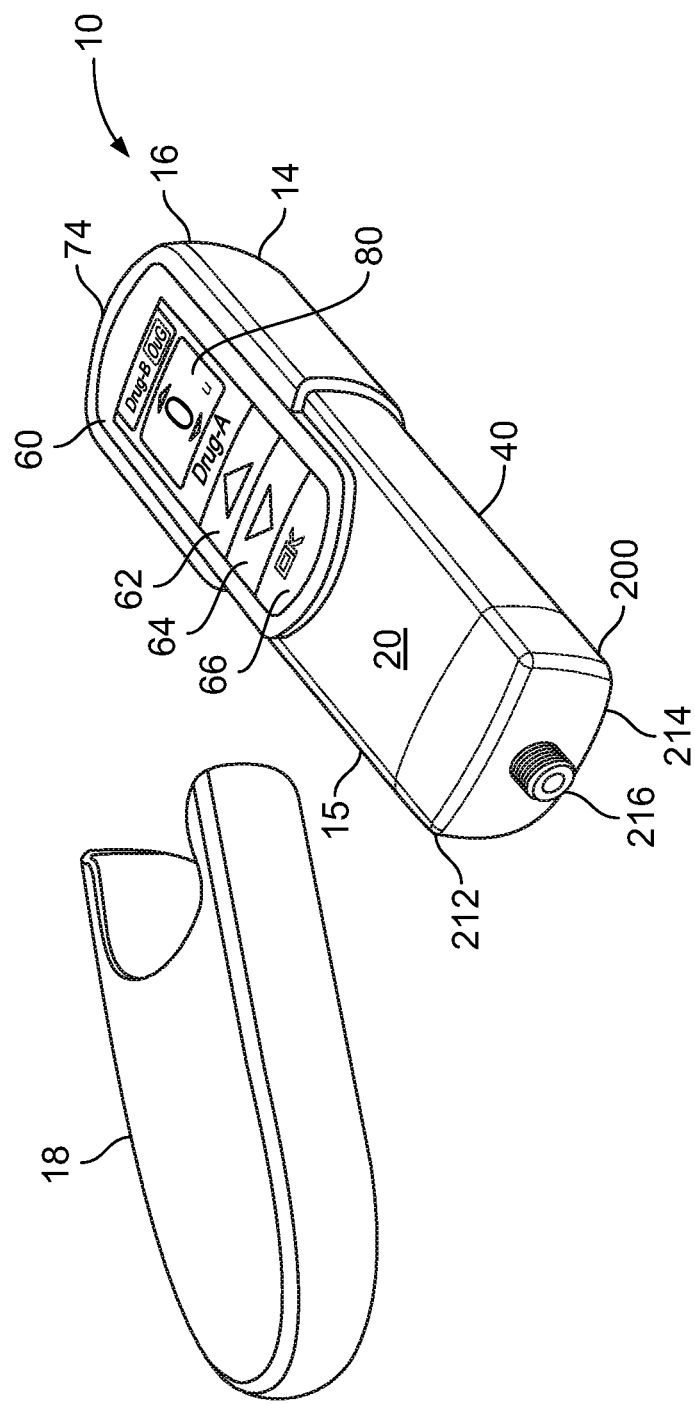
FIG. 1 illustrates a perspective view of a delivery device with an end cap of the device removed.
Figure 2:
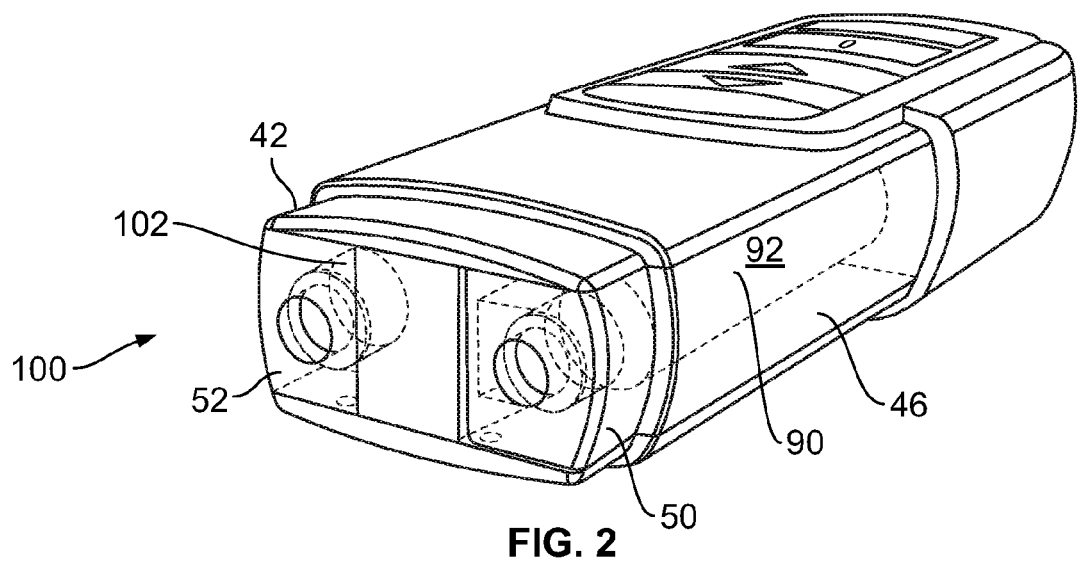
FIG. 2 illustrates a perspective view of the delivery device distal end showing the cartridge.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) can be attached to the interface. The drug delivery device 10 can be used to administer a computed dose of a second medicament (secondary drug compound) and a variable dose of a first medicament (primary drug compound) through a single needle assembly, such as a double ended needle assembly.

The drive train may exert a pressure on the bung of each cartridge, respectively, in order to expel the doses of the first and second medicaments. For example, a piston rod may push the bung of a cartridge forward a pre-determined amount for a single dose of medicament. When the cartridge is empty, the piston rod is retracted completely inside the main body 14, so that the empty cartridge can be removed and a new cartridge can be inserted.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1). The user interface of the drug delivery device may comprise additional buttons, such as a "menu" button, a "back" button, or a "light" button to switch on an illumination of the display.

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 210 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
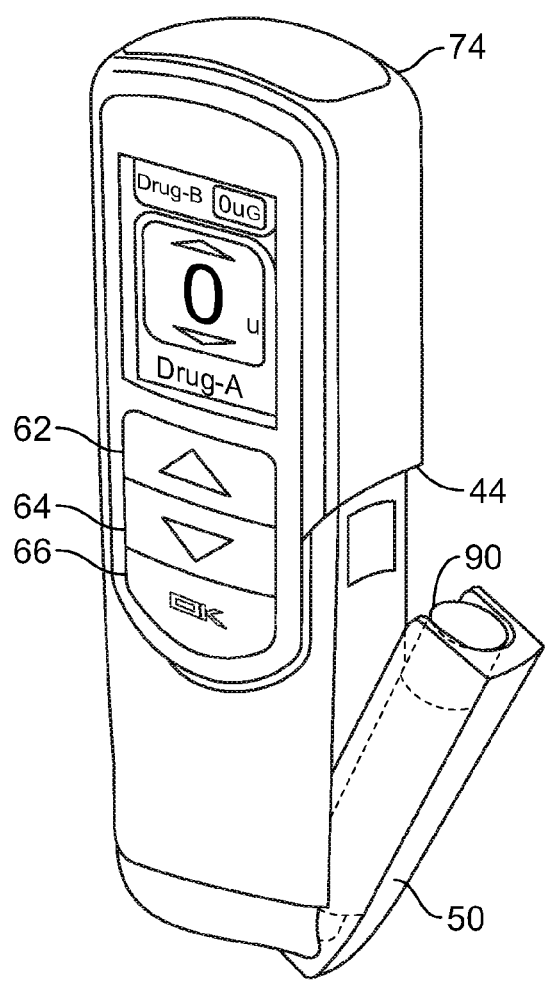
FIG. 3 illustrates a perspective view of the delivery device illustrated in FIG. 1 or 2 with one cartridge retainer in an open position.

As shown in FIG. 3, the first and second cartridge retainers 50, 52 may be hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
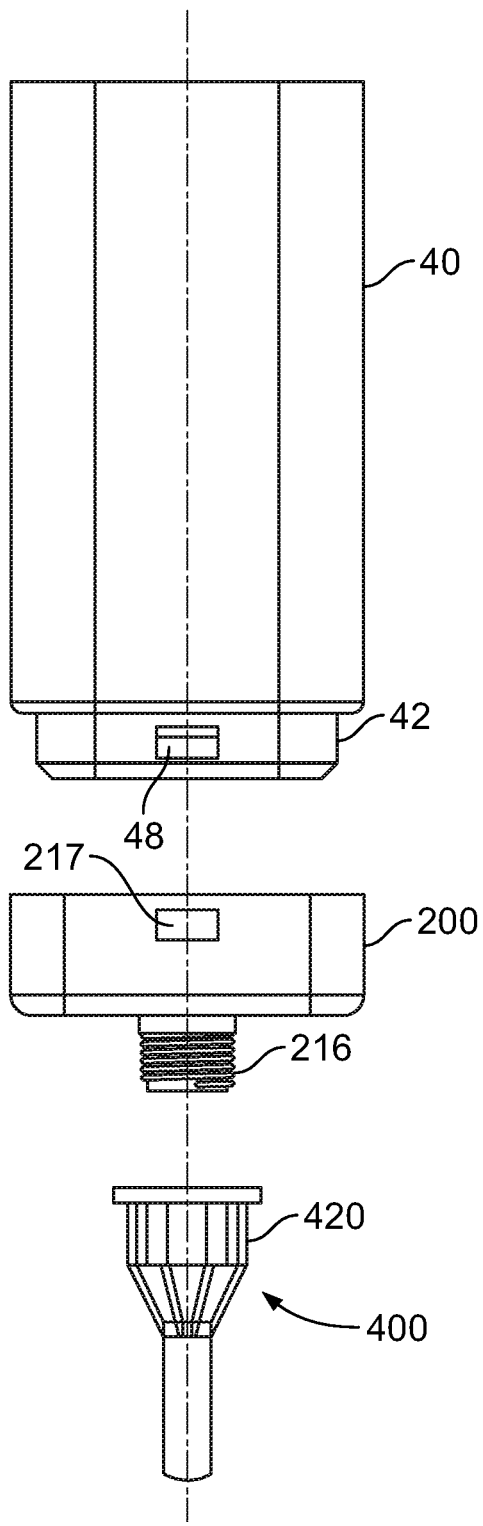
FIG. 4 illustrates a dispense interface and a dose dispenser that may be removably mounted on a distal end of the delivery device illustrated in FIG. 1.

As mentioned above when discussing FIG. 1, a dispense interface 200 can be coupled to the distal end of the cartridge holder 40. FIG. 4 illustrates a flat view of the dispense interface 200 unconnected to the distal end of the cartridge holder 40. A dose dispenser or needle assembly 400 that may be used with the interface 200 is also illustrated and is provided in a protective outer cap 420.

Figure 5:
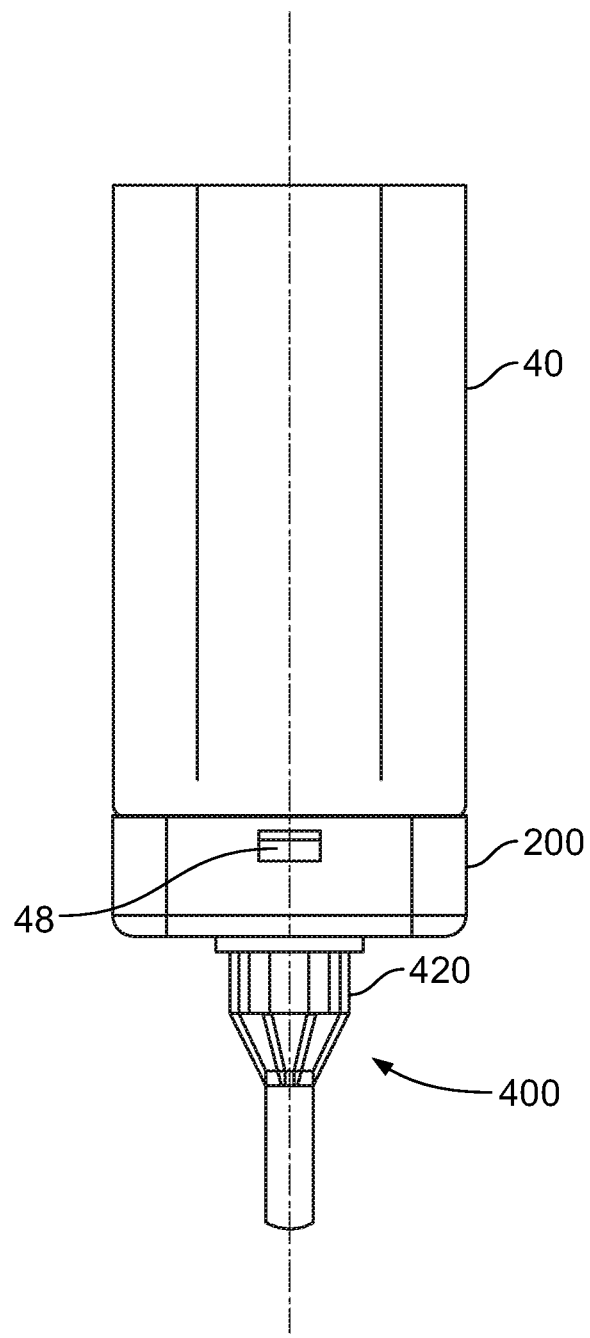
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means 48 between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
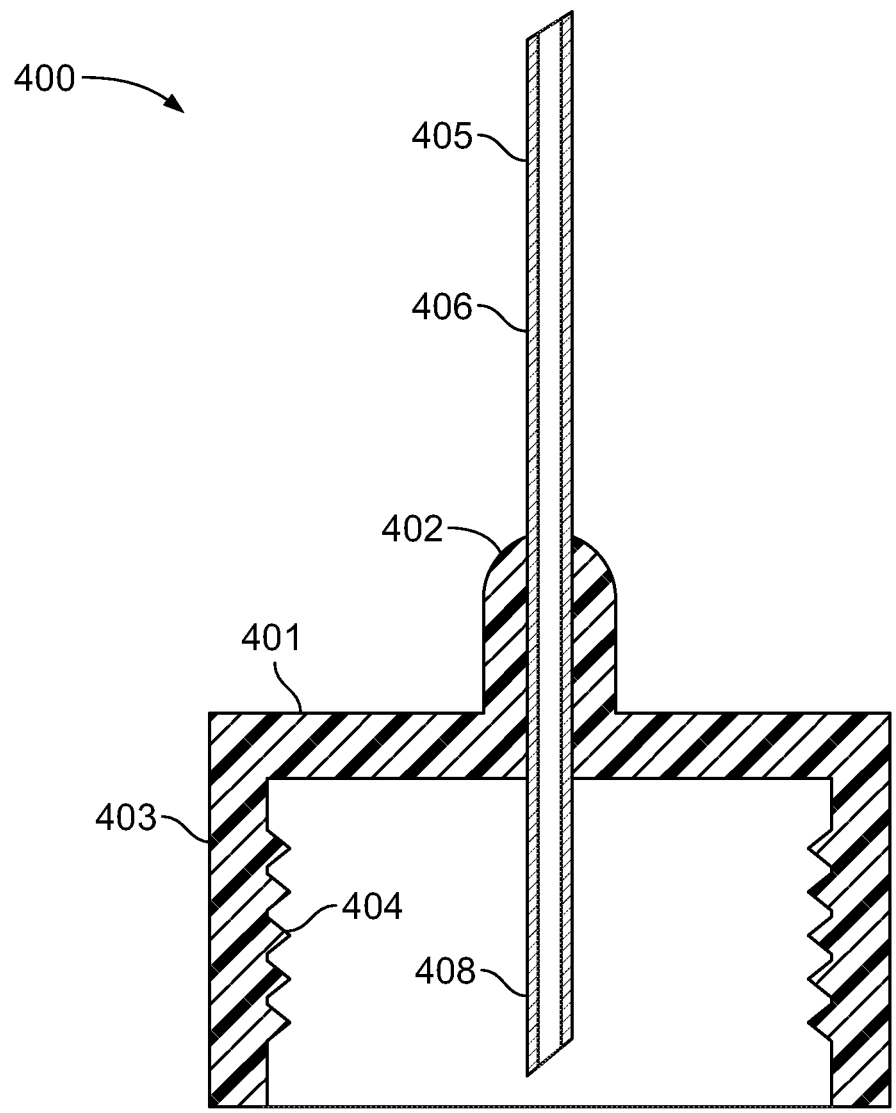
FIG. 6 illustrates one arrangement of a needle assembly that may be mounted on a distal end of the delivery device.
Figure 7:
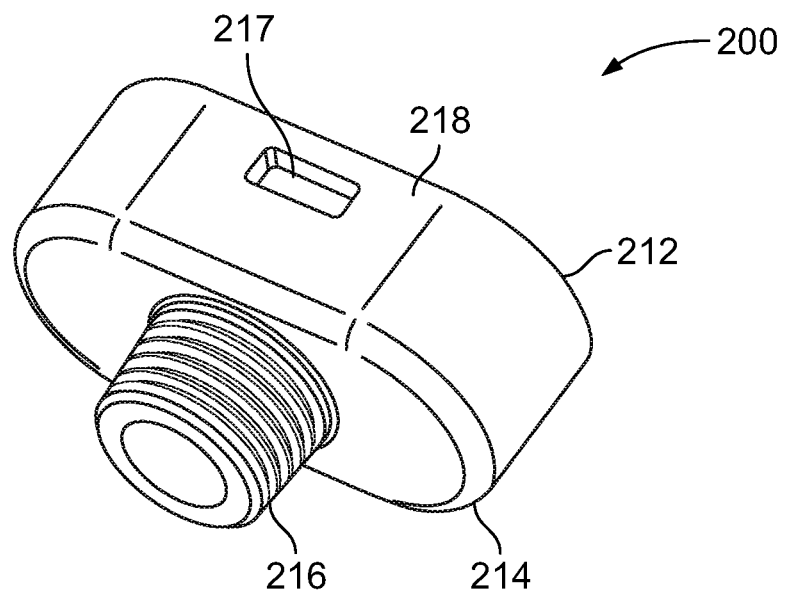
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 400 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 408 of the needle assembly 400 protrudes from an opposite side of the circular disc so that it is concentrically surrounded by the sleeve 403. In one needle assembly arrangement, the second or proximal piercing end 408 may be shorter than the sleeve 403 so that this sleeve to some extent protects the pointed end of the back sleeve. The needle cover cap 420 illustrated in FIGS. 4 and 5 provides a form fit around the outer surface of the hub 401.

Referring now to FIGS. 4 to 11, one preferred arrangement of this interface 200 will now be discussed. In this one preferred arrangement, this interface 200 comprises:
  a. a main outer body 210,
  b. an first inner body 220,
  c. a second inner body 230,
  d. a first piercing needle 240,
  e. a second piercing needle 250,
  f. a valve seal 260, and
  g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213a and a second rib 213b. This first rib 213a is also illustrated in FIG. 10. These ribs 213a and 213b are positioned along the inner surface 215 of the wall 218 of the outer body 210 and create a form fit or snap lock engagement with cooperating grooves 224a and 224b of the first inner body 220. In a preferred arrangement, these cooperating grooves 224*a* and 224*b* are provided along an outer surface 222 of the first inner body 220.

Figure 8:
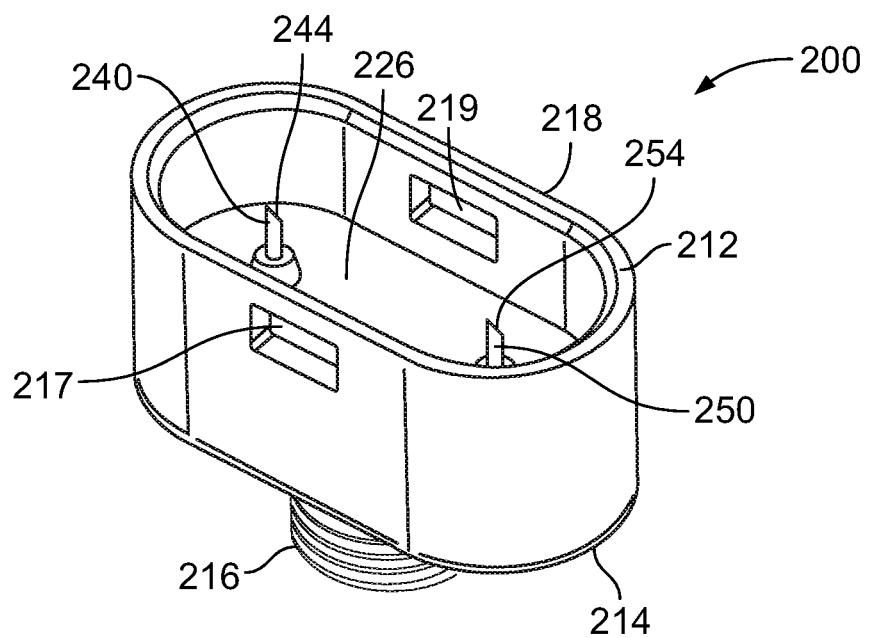
FIG. 8 illustrates another perspective view of the dispense interface illustrated in FIG. 4.
Figure 9:
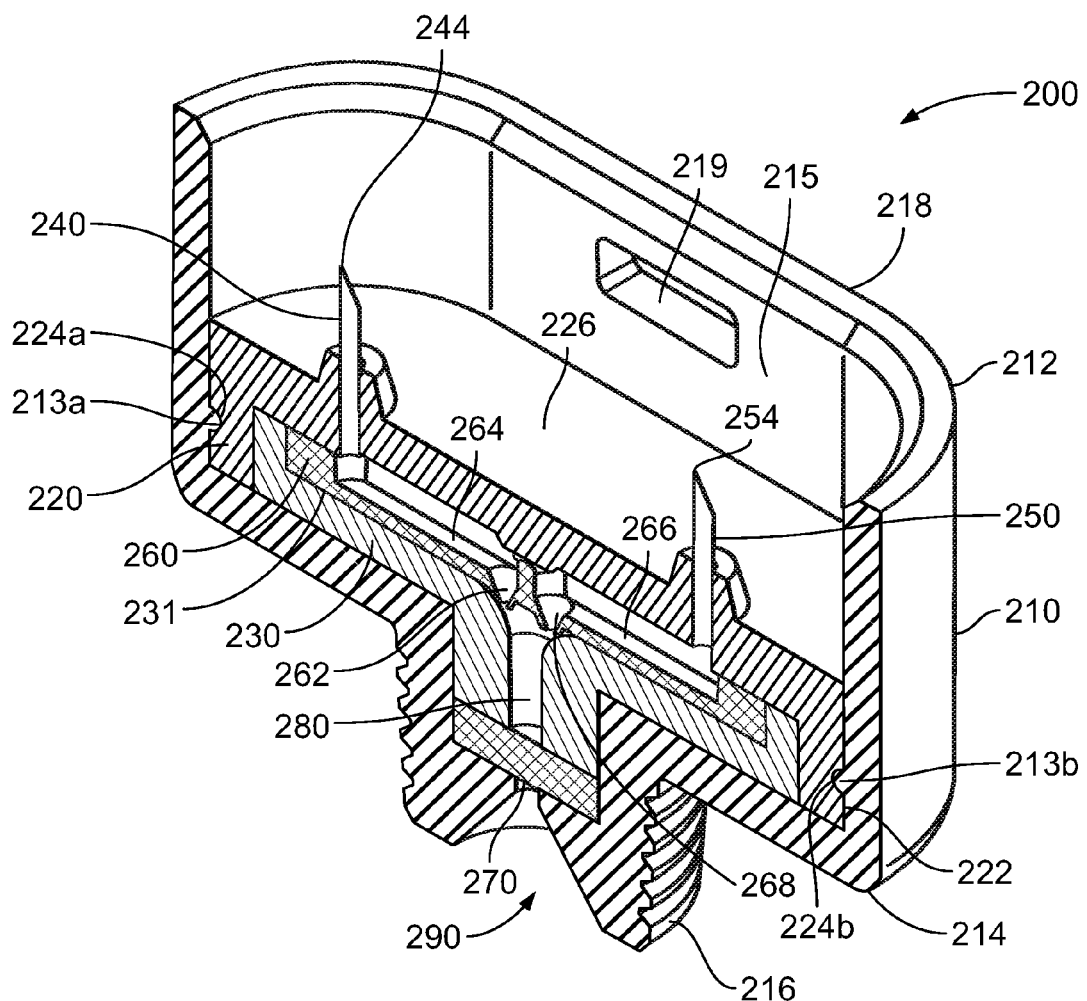
FIG. 9 illustrates a cross-sectional view of the dispense interface illustrated in FIG. 4.
Figure 10:
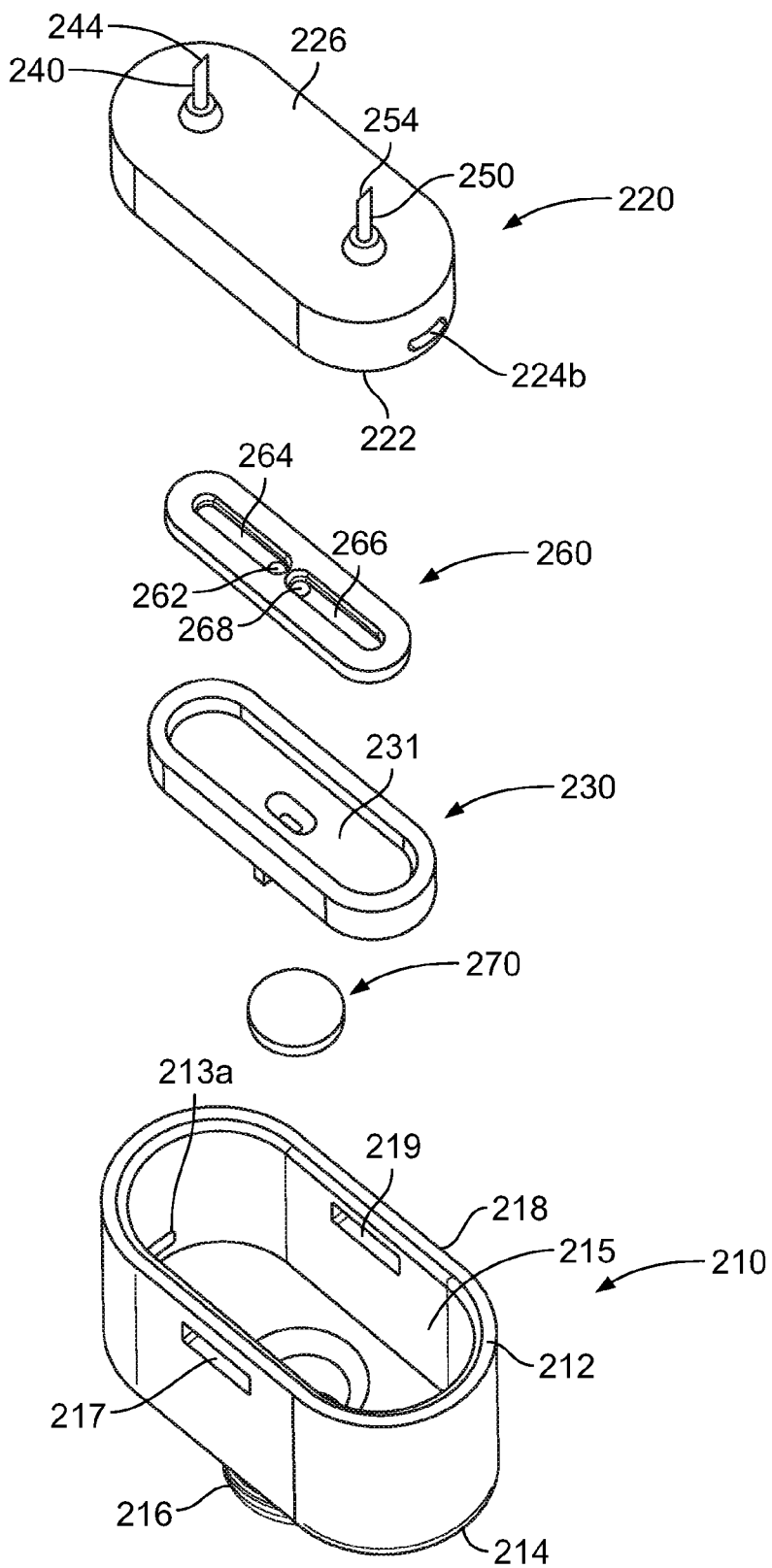
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
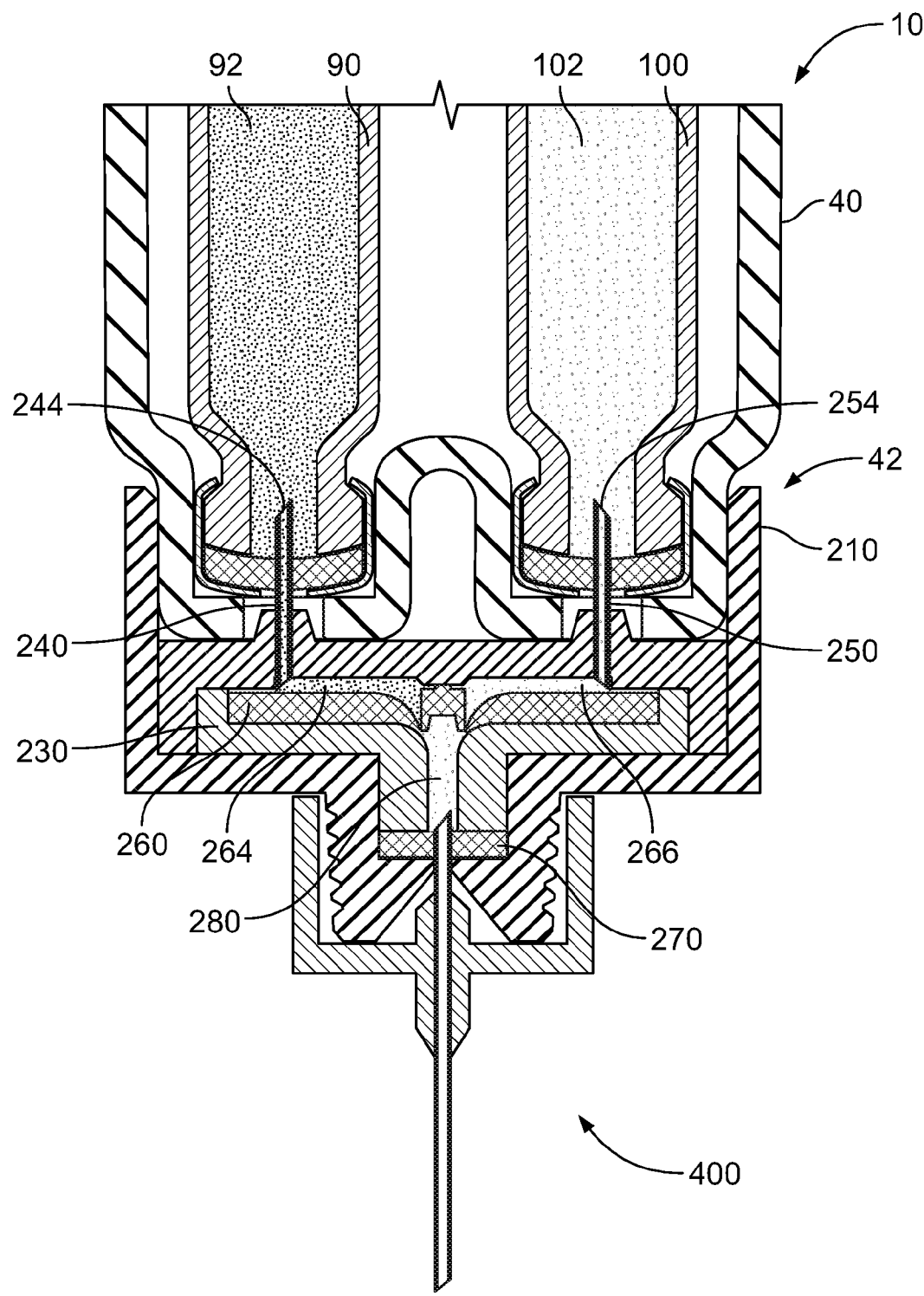
FIG. 11 illustrates a cross-sectional view of the dispense interface and needle assembly mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

Figure 12:
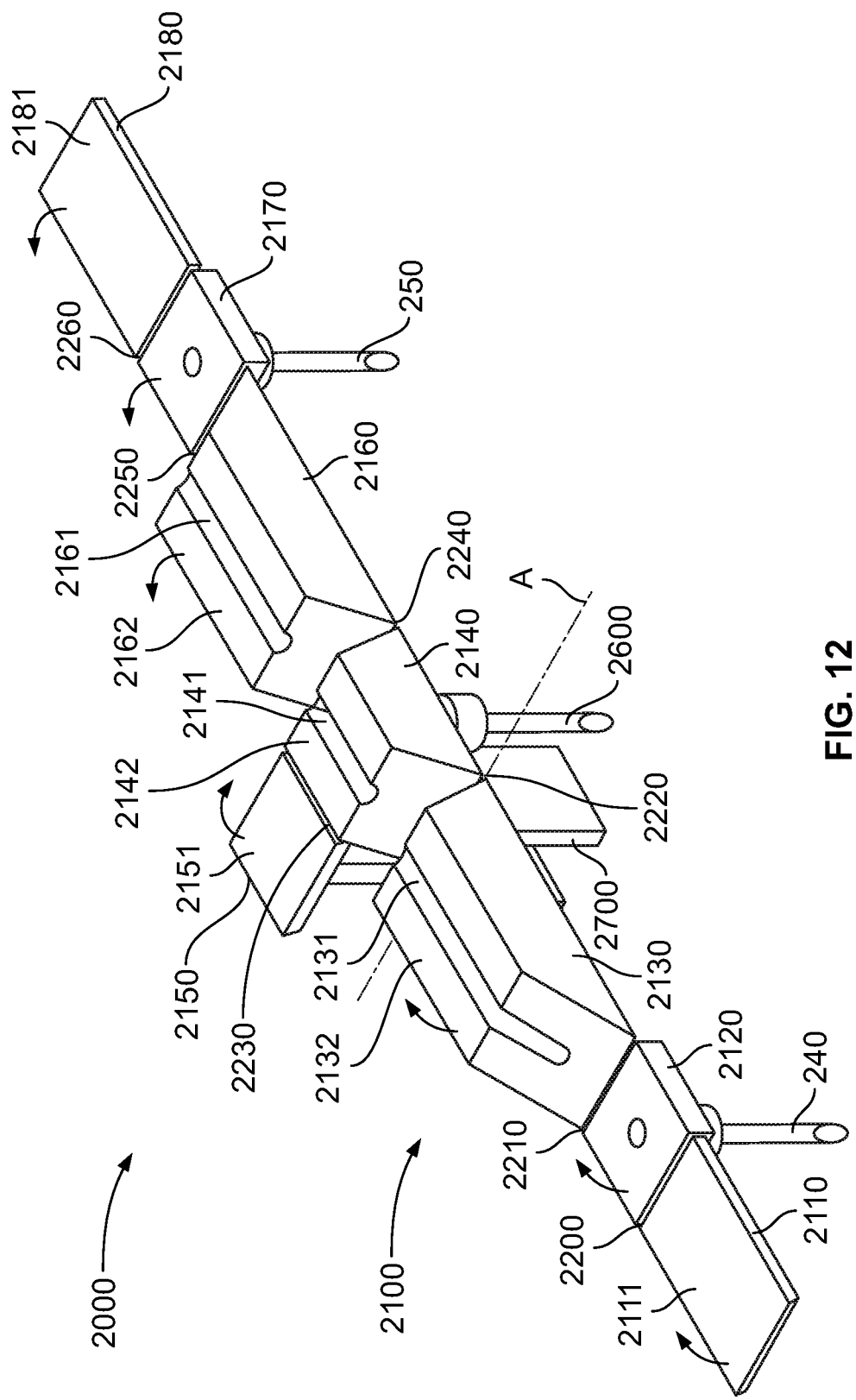
FIG. 12 illustrates a perspective view of an alternative embodiment of a dispense interface.
Figure 13:
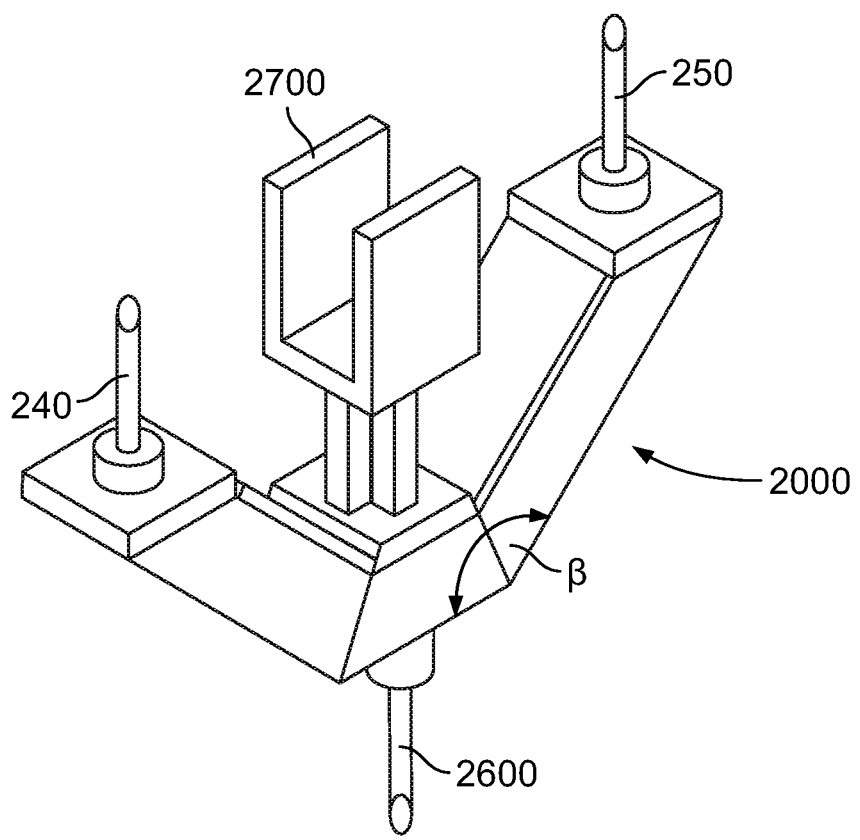
FIG. 13 illustrates another perspective view of the alternative embodiment of a dispense interface illustrated in FIG. 12.

FIGS. 12 to 13 illustrate an embodiment of a dispense interface 2000 alternative to the embodiment of the dispense interface 200 illustrated in FIGS. 7 to 11. In FIGS. 12 to 13 the same reference signs as in FIGS. 7 to 11 are used for parts which are similar. Furthermore, at this point, it is mainly referred to the above description of the embodiment of the dispense interface 200 illustrated in FIGS. 7 to 11 and, basically, the differences are described only.

As will now be discussed in greater detail, in one preferred arrangement, the dispense interface 2000 illustrated in FIGS. 12 to 13 comprises:

a. a part 2100 having multiple portions 2110, 2120, 2130, 2140, 2150, 2160, 2170, 2180;
   c. living hinges 2200, 2210, 2220, 2230, 2240, 2250, 2260;
   d. a first piercing needle 240;
   e. a second piercing needle 250;
   f. an optional valve arrangement (not illustrated);
   g. an injection needle 2600; and
   h. axial attachment means 2700.

One exemplary difference between the dispense interface 200 and the dispense interface 2000 is the outer shape. Nevertheless, the dispense interface 2000 is attachable to a drug deliver device by axial attachment means 2700 as described above.

As illustrated in FIG. 12, neighbouring portions of the multiple portions 2110, 2120, 2130, 2140, 2150, 2160, 2170 and 2180 are connected by respective living hinges 2200, 2210, 2220, 2230, 2240, 2250 and 2260. These multiple portions and living hinges are integrally formed from the same polymer material by injection moulding. Therein, the living hinges may be formed by pre-weakening the polymer material such that neighbouring portions of the multiple portions can be folded along the pre-weakening towards each other as indicated by the arrows in FIG. 12.

For instance, portions 2130 and 2140 are connected by living hinge 2220. For instance, living hinge 2220 has a rotational axis A. Accordingly, the material may be pre-weakened along the rotational axis A such that the portions 2130 and 2140 can be folded along the rotational axis A towards each other. For instance, the material is thinned along the rotational axis A.

The multiple portions comprise body portions 2130, 2140 and 2160 and cover portions 2110, 2150 and 2180. The body portions 2130, 2140 and 2160 comprise fluid grooves 2131, 2141 and 2161 arranged in their functional surfaces 2132, 2142 and 2162.

As apparent from FIG. 13, the fluid grooves 2131, 2141 and 2161 are sealed by functional surfaces 2111, 2151 and 2181 of the cover portions 2110, 2150 and 2180 facing the functional surfaces 2132, 2142 and 2162 of the body portions 2130, 2140 and 2160 when the multiple portions are folded towards each other. The multiple portions may be fixed by a material connection in this folded position. For instance, the multiple portions may be joined by laser welding at a mating/contact area.

In this folded position, the piercing needle 240 resides in fluid communication with the fluid groove 2131, and the piercing needle 250 resides in fluid communication with the fluid groove 2161. The fluid grooves 2131 and 2161 converge to the fluid groove 2141, to then provide for an output fluid path or the injection needle 2600.

Therein, the fluid groove 2141 resides in fluid communication with the injection needle 2600. Injection needle 2600 may be a cannula like needle 406. Alternatively, the fluid groove 2141 may reside in fluid connection with a fluid connector (e.g. a pierceable septum 270) such that needle assembly 400 or any other standard needle assembly may be attachable to the dispense interface 2000 (not illustrated).

Accordingly, dispense interface 2000 provides a fluid connection from piercing needle 240 and 250 to a common outlet such as injection needle 2600 when the multiple portions are folded towards each other.

The dispense interface 2000 may optionally comprise a valve arrangement such as one of the embodiments illustrated in FIGS. 14a to 14e. The function of such an optional valve arrangement may basically relate to the function of the first and second non return valve 262, 264 of the dispense interface 200. As described above, such a valve arrangement may for instance be constructed so as to prevent back flow and/or cross contamination of the first and second medicaments 92, 102 contained in the first and second reservoirs 90, 100, respectively. However, the dispense interface may also comprise no valve arrangement or a different valve arrangement.

As apparent from FIG. 13, the functional surfaces 2132, 2142 and 2162 of the body portions 2130, 2140 and 2160 are inclined to each other when the multiple portions are folded towards each other. The living hinge 2220 connecting body portions 2130 and 2140 is for instance arranged spaced from the functional surfaces 2132 and 2142 of the body portions 2130 and 2140. In particular, the facing surfaces of body portions 2130 and 2140 next to which the living hinge 2220 is arranged are inclined such that the functional surfaces 2132 and 2142 draw an (obtuse) angle β when the multiple portions are folded towards each other.

FIGS. 14a to 14e illustrate embodiments of a valve arrangement for a dispense interface such as the dispense interface 200 and 2000. In FIGS. 14a to 14e the same reference signs are used for parts which are similar.

The valve arrangement may for instance be integrally formed with another part of the dispense interface. Alternatively, the valve arrangement may for instance be manufactured separately from the other parts of the dispense interface.

For instance, the valve arrangement may be inserted (e.g. potted/over-moulded) into the multiple portions of the dispense interface 2000. For instance, the valve arrangement may at least partially be potted/over-moulded when the multiple portions are injection moulded. For instance, the valve arrangement may at least partially be mounted in a separate step after the multiple portions have been injection moulded.

Figure 14A:
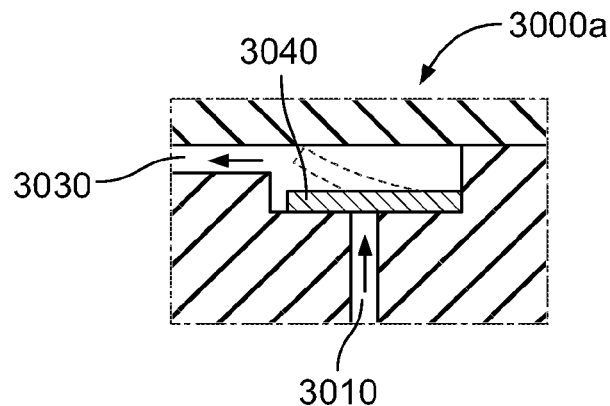
FIG. 14a illustrates an alternative embodiment of a valve arrangement of a dispense interface.

FIG. 14a illustrates a diaphragm/flap valve arrangement 3000a. The diaphragm/flap valve arrangement 3000a has an inlet 3010 and an outlet 3030. The inlet 3010 may for instance reside in fluid communication with one of the piercing needles 240, 250 of dispense interface 200 or 2000, and the outlet 3030 may for instance reside in fluid communication with holding chamber 280 of dispense interface 200 or injection needle 2600 of dispense interface 2000.

The diaphragm/flap valve arrangement 3000a has a flexible diaphragm/flap 3040. When the fluidic pressure in the inlet 3010 is increased (e.g. during a dose priming or a dose injecting step), the diaphragm/flap 3040 will change from an un-stressed state to a stressed state. In the stressed state, the fluidic pressure bends the diaphragm/flap 3040 as indicated by the arrow in FIG. 14a so that the diaphragm/flap valve arrangement 3000a opens. In this stressed condition, the diaphragm/flap valve arrangement 3000a will allow fluid to flow from the inlet 3010 to the outlet 3030. When the fluidic pressure in the inlet is removed, the diaphragm/flap 3040 will return to its initial position and seal the inlet 3010, preventing backflow.

Figure 14B:
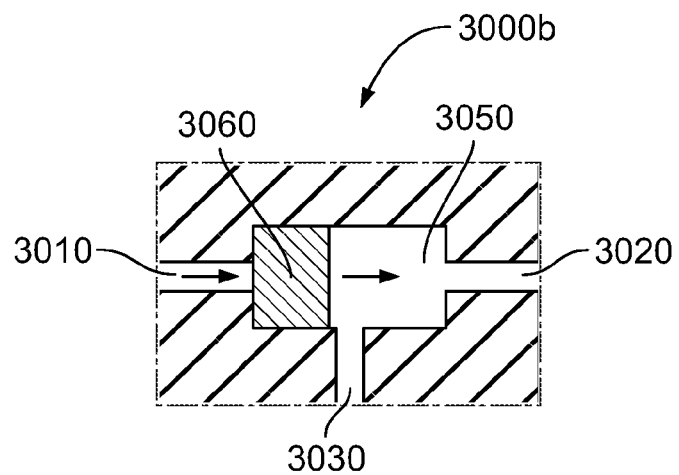
FIG. 14b illustrates another alternative embodiment of a valve arrangement of a dispense interface.

FIG. 14b illustrates a shuttling valve arrangement 3000b. The shuttling valve arrangement 3000b has a tube 3050. The tube 3050 has two inlets 3010, 3020 and an outlet 3030. The inlet 3020 may also reside in fluid communication with one of the piercing needles 240, 250 of dispense interface 200 or 2000. In the tube 3050 a movable element 3060 (e.g. a piston or a ball) is arranged.

The diameter of the movable element 3060 corresponds to the diameter of the tube 3050 such that the movable element 3060 is movable between a first and a second (longitudinal) position in the tube 3050. In the first position (illustrated in FIG. 14b), the movable element 3060 seals the inlet 3010 and allows fluid to flow from the inlet 3020 to the outlet 3030. In the second position (not illustrated), the movable element 3060 seals the inlet 3020 and allows fluid to flow from the inlet 3010 to the outlet 3030. When the fluidic pressure in the inlet 3010 is for instance increased (e.g. during a dose priming or a dose injecting step), the movable element 3060 will be pushed towards the second position as indicated by the arrow in FIG. 14b.

Figure 14C:
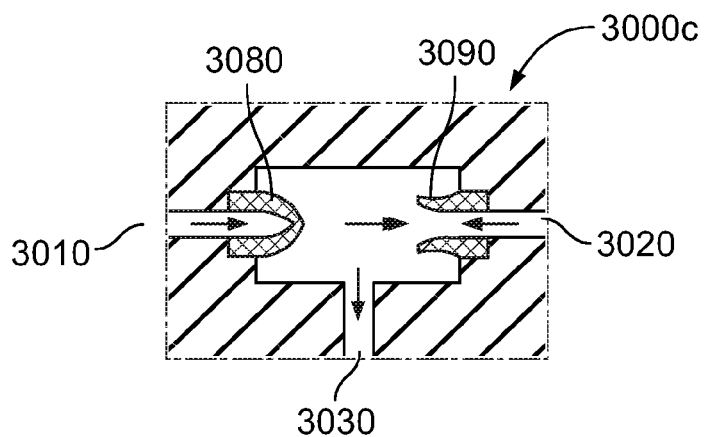
FIG. 14c illustrates another alternative embodiment of a valve arrangement of a dispense interface.

FIG. 14c illustrates a moulded duckbill valve arrangement 3000c. The moulded duckbill valve arrangement 3000c has a first and a second duckbill valve 3080, 3090. When the fluidic pressure in the inlet 3020 is increased (e.g. during a dose priming or a dose injecting step), the second duckbill valve 3090 will change from an un-stressed state to a stressed state. In the stressed state, the fluidic pressure inverts the naturally flattened shape of the duckbill valve as indicated in FIG. 14c so that the duckbill valve opens. In this stressed condition, the second duckbill valve 3090 will allow fluid to flow from the inlet 3020 to the outlet 3030. When the fluidic pressure in the inlet 3020 is removed, the second duckbill valve 3090 will return to its flattened shape and seal the inlet 3020, preventing backflow. The first duckbill valve 3080 operates in a similar manner as the second duckbill valve 3090 when the fluidic pressure is increased in the inlet 3010.

Figure 14D:
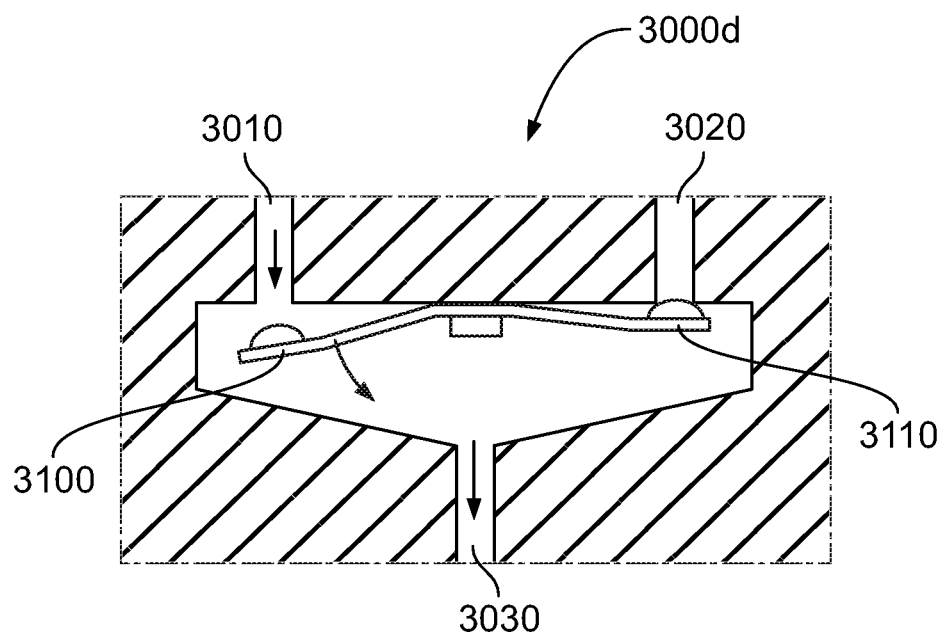
FIG. 14d illustrates another alternative embodiment of a valve arrangement of a dispense interface.

FIG. 14d illustrates a flat spring valve arrangement 3000d. The flat spring valve arrangement 3000d has a first and a second flat spring 3100, 3110. The first and the second flat spring 3100, 3110 may for instance be integrally formed.

When the fluidic pressure in the inlet 3010 is increased (e.g. during a dose priming or a dose injecting step), the first flat spring 3100 will change from an un-stressed state to a stressed state. In the stressed state, the fluidic pressure bends the first flat spring 3100 as indicated by the arrow in FIG. 14d so that the flat spring valve arrangement 3000d opens. In this stressed condition, the flat spring valve arrangement 3000d will allow fluid to flow from the inlet 3010 to the outlet 3030. When the fluidic pressure in the inlet 3010 is removed, the first flat spring 3100 will return to its initial position and seal the inlet 3010, preventing backflow. The second flat spring 3110 operates in a similar manner as the first flat spring 3100 when the fluidic pressure is increased in the inlet 3020.

Figure 14E:
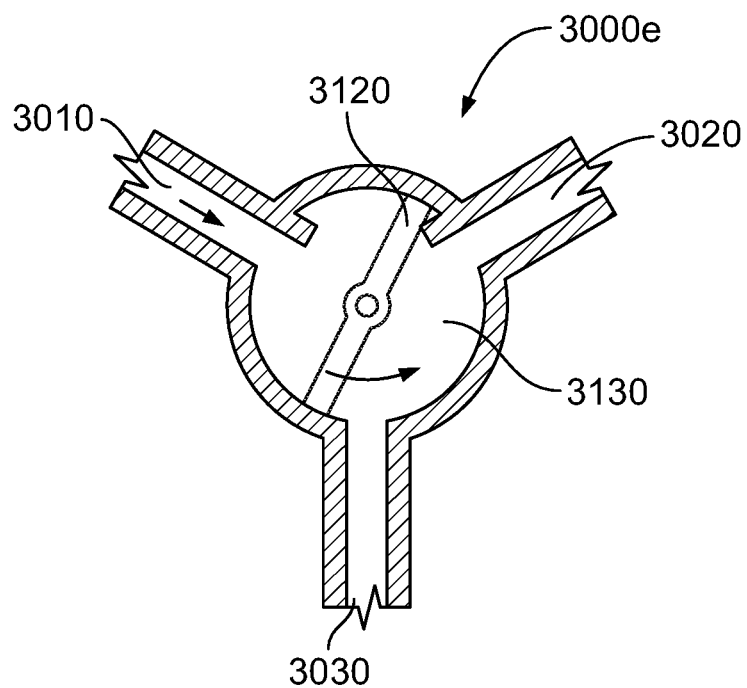
FIG. 14e illustrates another alternative embodiment of a valve arrangement of a dispense interface.

FIG. 14e illustrates a rotating flap valve arrangement 3000e. The rotating flap valve arrangement 3000e has a flap 3120 which is rotatably mounted in a valve chamber 3130. The valve chamber has two inlets 3010, 3020 and an outlet 3030.

The flap 3120 is rotatable between a first and a second position. In the first position (illustrated in FIG. 14e), the flap 3120 seals the inlet 3010 and allows fluid to flow from the inlet 3020 to the outlet 3030. In the second position (not illustrated), the flap 3120 seals the inlet 3020 and allows fluid to flow from the inlet 3010 to the outlet 3030.

When the fluidic pressure in the inlet 3010 is for instance increased (e.g. during a dose priming or a dose injecting step), the flap 3120 will be pushed towards the second position as indicated by the arrow in FIG. 14e.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
 H-(Lys)4-des Pro36, des Pro37 Exendin-4(1-39)-NH2,
 H-(Lys)5-des Pro36, des Pro37 Exendin-4(1-39)-NH2,
 des Pro36 [Asp28] Exendin-4(1-39),
 des Pro36 [IsoAsp28] Exendin-4(1-39),
 des Pro36 [Met(O)14, Asp28] Exendin-4(1-39),
 des Pro36 [Met(O)14, IsoAsp28] Exendin-4(1-39), des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two 0 sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A dispense interface for an ejection device, said dispense interface comprising:
at least two inlets;
at least one outlet; and
a part comprising multiple integral portions;
wherein said multiple integral portions are connected by integral living hinges such that said multiple integral portions are foldable towards each other;
wherein said multiple integral portions are configured to form a fluid channel arrangement between functional surfaces of said multiple integral portions facing each other when said multiple integral portions are folded towards each other;
wherein said functional surfaces are outer surfaces of said multiple integral portions prior to said multiple integral portions being folded towards each other;
wherein at least two functional surfaces of said functional surfaces are inclined to each other when said multiple integral portions are folded towards each other into a folded position; and
wherein said fluid channel arrangement comprises at least one fluid groove arranged on at least one functional surface of said functional surfaces so as to provide fluid communication between said at least two inlets and said at least one outlet when said multiple integral portions reside in the folded position.

2. The dispense interface according to claim 1, wherein each of said at least two inlets is formed from a fluid connector emptying into said fluid channel arrangement, and wherein each of said fluid connectors is configured to establish a releasable fluid connection with a corresponding fluid connector of a fluid reservoir of said ejection device when said dispense interface is attached to said ejection device.

3. The dispense interface according to claim 1, wherein said at least one outlet is formed from a fluid connector, wherein said fluid channel arrangement empties into said fluid connector, and wherein said fluid connector is configured to establish a fluid connection with a corresponding fluid connector of a needle assembly, when said needle assembly is attached to said dispense interface.

4. The dispense interface according to claim 1, wherein said at least one outlet is formed from a needle, and wherein said fluid channel arrangement empties into said needle.

5. The dispense interface according to claim 1, said dispense interface further comprising:
a valve arrangement configured to control a fluid flow from said at least two inlets to said at least one outlet via said fluid channel arrangement.

6. The dispense interface according to claim 1, wherein said multiple integral portions are folded towards each other, and wherein said multiple integral portions are fixed in the folded position by at least one of a mechanical connection and a material connection.

7. The dispense interface according to claim 1, wherein said multiple integral portions comprise at least two body portions and at least two cover portions, and wherein each fluid channel of said fluid channel arrangement is formed between a functional surface of a respective body portion of said at least two body portions and a functional surface of a respective cover portion of said at least two cover portions when said multiple integral portions are folded towards each other.

8. The dispense interface according to claim 7, wherein at least one living hinge of said living hinges connecting two body portions of said at least two body portions is spaced from said functional surfaces of the two body portions.

9. The dispense interface according to claim 1, wherein said part having said multiple integral portions is integrally formed by an injection moulding.

10. A method for manufacturing the dispense interface according to claim 1, said method comprising:
moulding the part comprising multiple integral portions;
folding said integral multiple portions towards each other; and
fixing said integral multiple portions in the folded position.

11. The method according to claim 10, wherein fixing said multiple integral portions in the folded position comprises at least one of: (i) gluing said multiple integral portions to each other in the folded position, or (ii) welding said multiple integral portions to each other in the folded position.

12. A system, comprising
the dispense interface according to claim 1; and
the ejection device;
wherein said dispense interface is attached to said ejection device.

13. The system according to claim 12, said system further comprising:
a needle assembly;
wherein said needle assembly is attached to said dispense interface.

14. The system according to claim 12, wherein said ejection device is a medical device configured to eject a medicament.

15. A method for using the system according to claim 12, said method comprising:
attaching the dispense interface to the ejection device, wherein the ejection device has at least two fluid reservoirs;
ejecting a fluid from at least one of the reservoirs through said dispense interface; and
detaching said dispense interface from said ejection device.

16. The dispense interface according to claim 1, wherein the at least two functional surfaces of said functional surfaces are inclined at an obtuse angle relative to each other when said multiple integral portions are in the folded position.

17. The dispense interface according to claim 1, wherein said multiple integral portions comprise more than two integral portions, and
wherein the integral living hinges comprise more than one integral living hinge.

18. The dispense interface according to claim 1, wherein the fluid channel arrangement is Y-shaped when the multiple integral portions are in the folded position.

19. The dispense interface according to claim 1, wherein said multiple integral portions comprise a body portion and a cover portion,
wherein the at least one fluid groove is on the outer surface of the body portion, and
wherein the cover portion laterally seals the at least one fluid groove on the body portion when the cover portion is folded toward the body portion to form the fluid channel arrangement between the cover portion and the body portion.

20. The dispense interface according to claim 19, wherein a ratio between a length of the fluid channel arrangement and a diameter of the fluid channel arrangement is greater than a ratio of 20:1.

* * * * *